United States Patent
Mutter et al.

(10) Patent No.: US 6,790,935 B1
(45) Date of Patent: Sep. 14, 2004

(54) CYCLOSPORIN DERIVATIVES AND METHOD FOR THE PRODUCTION OF SAID DERIVATIVES

(75) Inventors: Manfred Mutter, Préverenges (CH); Roland Wenger, Richen (CH); Jean-François Guichou, Lausanne (CH); Michael Keller, London (GB); Thomas Ruckle, Lausanne (CH); Torsten Woehr, Zürich (CH)

(73) Assignee: Debiopharm S.A., Lausanne (CH)

( * ) Notice: Subject to any disclaimer, the term of this patent is extended or adjusted under 35 U.S.C. 154(b) by 0 days.

(21) Appl. No.: 09/890,636

(22) PCT Filed: Feb. 7, 2000

(86) PCT No.: PCT/IB00/00133

§ 371 (c)(1),
(2), (4) Date: Aug. 30, 2001

(87) PCT Pub. No.: WO00/46239

PCT Pub. Date: Aug. 10, 2000

(30) Foreign Application Priority Data

Feb. 5, 1999 (CH) .............................................. 220/99

(51) Int. Cl.[7] .............................................. C07K 7/50
(52) U.S. Cl. .......................... 530/317; 530/327; 514/11; 514/15
(58) Field of Search ................................ 530/317, 327; 514/11, 15, 374; 548/215; 562/553

(56) References Cited

FOREIGN PATENT DOCUMENTS

| EP | 0 034 567 | 8/1981 |
|---|---|---|
| EP | 0 300 785 | 1/1989 |
| GB | 2 205 317 | 12/1988 |
| WO | WO 00/01715 | 1/2000 |

OTHER PUBLICATIONS

Chem Abstr 127, 95603, 1998.*

Traber et al, *The Journal of Antibiotics*, 1989, 42, 591–7 "Cyclosporins –New Analogues by Precursor Directed Biosynthesis.".

Fisher et al, *Biomed. Biochem. Acta*, 1984, 43, 1101–11 "Detection of enzyme catalysis for cis–trans–isomerisation of peptide bonds using proine–containing peptides as substracts.".

Wöhr et al., *J. Am. Chem. Soc.*, 1996, 118, 9218–27, "Pseudo–prolines as a solubilizing, structure–disrupting protection technique in peptide synthesis."

Dumy et al., *J. Am. Chem. Soc.*, 1997, 119, 918–25, "Pseudo–prolines as a molecular hinge: reversible induction of cis amide bonds into peptide backbones."

Keller et al, *J. Am. Chem. Soc.*, 1998, 120, 2714–20, "Enhancing the proline effect: pdeudo–prolines for tailoring cis/trans isomerization."

* cited by examiner

Primary Examiner—Christopher S. F. Low
Assistant Examiner—David Lukton
(74) Attorney, Agent, or Firm—Nixon & Vanderhye, P.C.

(57) ABSTRACT

The invention relates to cyclosporin derivatives, whereby the peptide chain thereof comprises at least one pseudo-proline type non-natural amino acid radical. The invention also relates to a method for the production of said derivatives.

15 Claims, 3 Drawing Sheets

CYCLOSPORIN DERIVATIVES AND METHOD FOR THE PRODUCTION OF SAID DERIVATIVES

This application is the U.S. national phase of international application PCT/IB00/00133 filed Feb. 7, 2000, which designates the U.S., the entire content of which is incorporated herein by reference.

The present invention relates to cyclosporin derivatives in which the peptide sequence comprises at least one non-natural amino acid of the pseudo-proline type. It also relates to a method of preparing the said derivatives.

Cyclosporins constitute a family of secondary metabolites obtained by fermentation. These substances possess remarkable biological properties, including immunosuppression, and the ability to induce nerve proliferation in neurodegenerative diseases or to stop replication of the HIV-1 virus. About thirty cyclosporins have so far been isolated from natural sources. The best known, on account of its use in organ transplantation, is Cyclosporin A (CsA). It was subsequently found that the same Cyclosporin A might open up new pathways in the treatment of AIDS by inhibiting activation of the $CD4^+$ cells.

Cyclosporins consist of a complex cyclic peptide sequence of eleven amino acids, some of these being non-natural amino acids that are frequently methylated on the nitrogen atom. These substances are strongly hydrophobic in character, which complicates their administration in a physiological medium.

At present, there is still a need to modify the structure in order to improve the biological activity and/or physico-chemical properties of the existing cyclosporins, whether natural or synthetic.

One of the aims of the present invention, therefore, is to make available cyclosporin derivatives of natural or synthetic origin, in which the pharmacological specificity has been improved, preferably to favor inhibition of $CD4^+$ cell activation so as to stop replication of the HIV-1 virus.

Another aim of the present invention is to make available cyclosporin derivatives, of natural or synthetic origin, of which the physical properties have been modified so as to confer on them a certain hydrophilic character, in order to increase their solubility in a physiological medium and so to facilitate their administration.

DETAILED DESCRIPTION OF THE INVENTION

Figure 1:
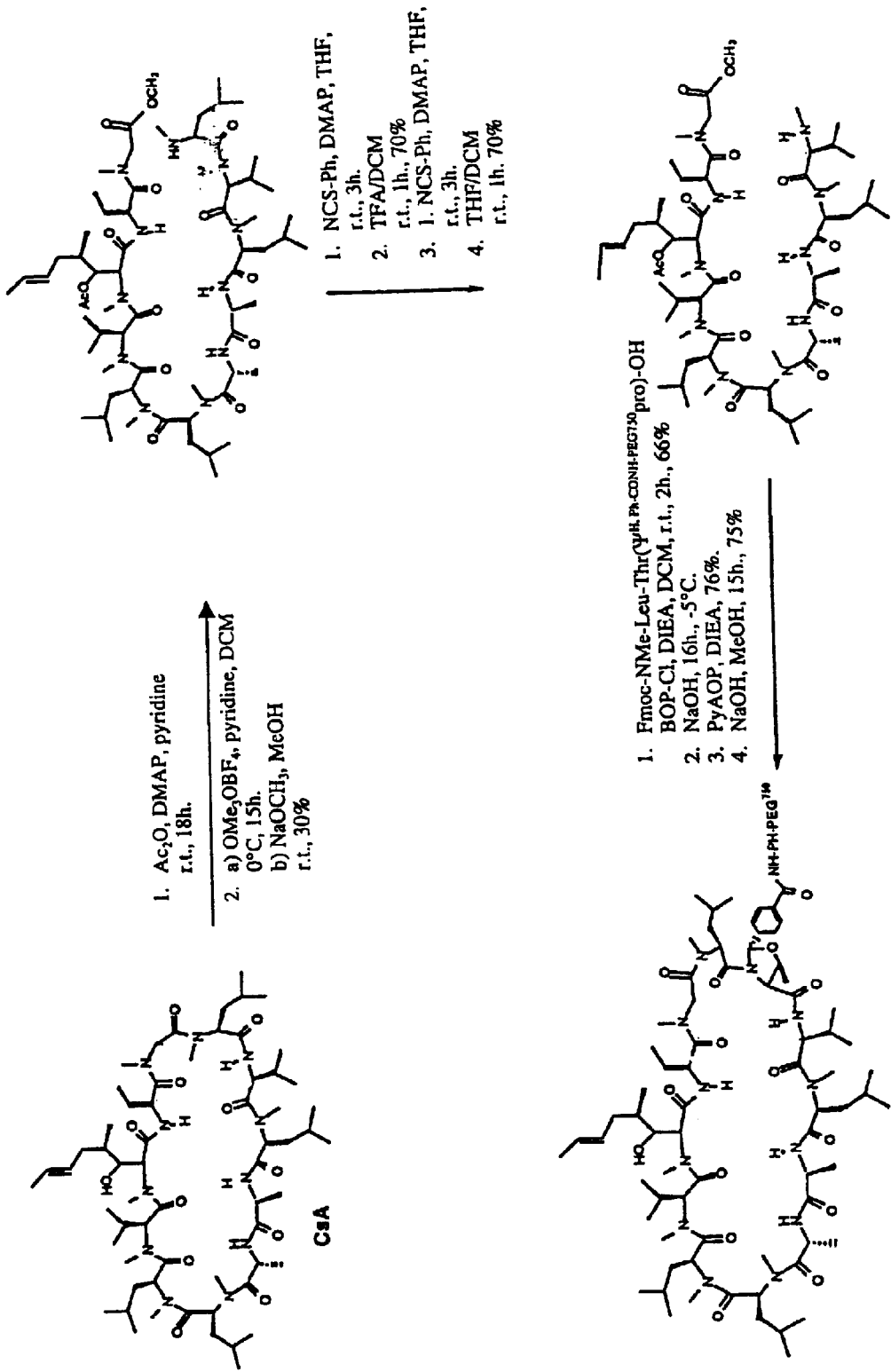
FIG. 1 shows the synthetic scheme for the synthesis of a cyclosporin derivative.

The object of the present invention is therefore cyclosporin derivatives of natural or non-natural origin, in which the peptide chain of the said derivatives comprises at least one non-natural amino acid residue of general formula I:

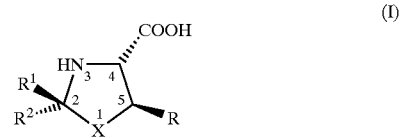

in which

X represents an oxygen or sulfur atom;

R represents a hydrogen atom or an alkyl group containing between 1 and 6 carbon atoms, preferably a methyl group;

$R_1$ and $R_2$ represent, independently of each other, a hydrogen atom, an alkyl group, containing between 1 and 6 carbon atoms, that may be straight-chain or branched-chain, substituted or non-substituted, an alkylene group containing between 1 and 6 carbon atoms, a non-substituted aryl group such as phenyl, a substituted aryl group such as p-carbomethoxyphenyl or p-methoxyphenyl, or a substituted or non-substituted heteroaryl group.

$R^1$ and $R_2$ may also represent a residue of a water-soluble polymer, possibly bound to a spacer group. Suitable examples of such a polymer include polyalkylene oxides (PAO) such as polyethylene glycols, polyvinyl alcohols, and carbohydrate-based polymers. The water-soluble polymer is preferably a polyalkylene oxide, such as a polyethylene glycol. The spacer group may be an alkyl group containing between 1 and 6 carbon atoms, an aryl group such as phenyl, or a heteroaryl, each carrying a functional group permitting anchoring to the polymer. If the polymer is a polyethylene glycol the preferred spacer group is p-carboxyphenylene.

The generic name "pseudo-proline" has been given in the present application to the non-natural amino acid of general formula I, and the abbreviations $Ser(\Psi^{R1,R2}pro)$, $Thr(\Psi^{R1,R2}pro)$ and $Cys(\Psi^{R1,R2}pro)$ indicate that, in the general formula I, the symbols (X, R) represent respectively (O, H), (O, Me) and (S, H), and that the amino add is derived respectively from serine, threonine and cysteine.

The cyclosporin derivatives of the present invention are preferably derived from natural or synthetic cyclosporins in which the peptide chain contains at least one of the following amino acids in the d or l configuration: serine, threonine or cysteine. In the peptide sequence of the cyclosporin derivatives of the present invention, at least one of the amino acids serine, threonine or cysteine, in the d or l configuration, of the basic cyclosporins has been replaced by a non-natural amino acid of general formula I.

On account of the complexity of the peptide chain of the cyclosporins, any chemical modification of their structure rapidly becomes complicated. For this reason, a total synthesis is not considered suitable.

Therefore, another aim of the present invention is to provide the simplest possible preparative method for these cyclosporin derivatives, using starting materials, both cyclosporins and reagents, which are easily available.

Thus the object of the present invention is also to provide a method of preparation of cyclosporin derivatives in which the peptide chain comprises at least one of the amino adds serine, threonine and cysteine, by N,O-acetalisation of at least one of the three above-mentioned amino acids. This is done by bringing the cyclosporin into contact with a compound of formula II:

(II)

in which

Z$_1$ and Z$_2$ represent, independently of each other, a halogen, a hydroxyl group, an alkoxy group, a thiol; or both Z$_1$ and Z$_2$ represent either an oxygen of a carbonyl group or a sulfur of a thione; and R$_1$ and R$_2$ have the same definition as above.

The compound of formula II is preferably an acetal or thioacetal.

The properties of the cyclosporin derivatives of the present invention, the advantages offered by them, and the detailed method of preparation of these derivatives will be illustrated using the specific examples below, and with the help of the drawings.

Three cyclosporins served as the starting materials for preparation of the derivatives by the method of the invention. Two of these cyclosporins are of natural origin. These are Cyclosporin A (CsA) and Cyclosporin C (CsC). The third cyclosporin, [D-Ser$^8$]Cyclosporin A, is obtained by fermentation with incorporation of the amino acid D-serine, according to the method described by Traber et al. in *The Journal of Antibiotics*, 1989.

Two series of experiments were performed, depending on the nature of the cyclosporin derivatives prepared. The first series of experiments was directed towards modification of the physical properties of the cyclosporins, and particularly towards the conferring of hydrophilic character. The second series focused on improvement of their biological properties.

In this connection, it is known from well-established structure-activity studies that the continuous peptide moiety in Cyclosporin A constituted by the amino acids in positions 10 to 11, 1 to 3 (the numbering system takes the amino acid MeBmt as position 1) binds to cyclophilin (CyP), a protein having peptidylprolyl cis-trans isomerase activity. The free peptide part then binds to calcineurin (Cn) and the complex so formed [(CsA-CyP)-Cn] is responsible for immunosuppression, as it inhibits transcription of the essential genes of the cytokines. The structure of Cyclosporin C is distinguished from that of Cyclosporin A by the amino acid in position 2, which is Ser instead of Abu. Its mode of action is similar, however.

1. Preparation of the derivatives of Cyclosporin A, i.e., [5-L-Thr($\Psi^{R1,R2}$pro)]CsA of general formula III:

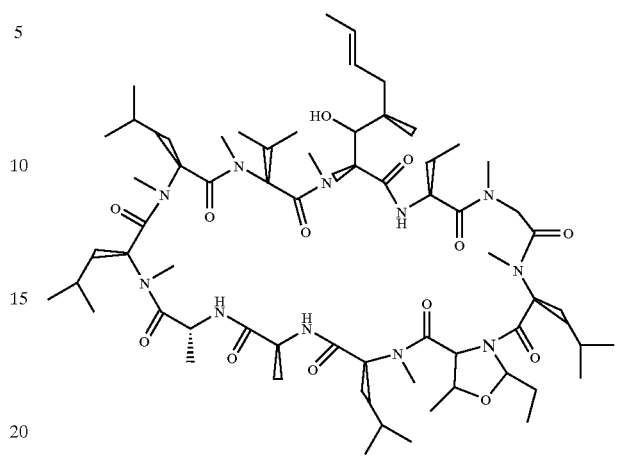
(III)

In derivatives of Cyclosporin A of general formula III, pseudo-proline L-Thr($\Psi^{R1,R2}$pro) occupies position 5, thus substituting the valine of Cyclosporin A.

This is achieved by opening the Cyclosporin A ring by cleavage of the 4–5 peptide bond. The 7–8 peptide bond is then cleaved in turn. After the protection and activation stages the dipeptide Fmoc-NMeLeu-L-Thr($\Psi^{R1,R2}$pro)-OH, prepared previously, is bound to the aminoacid Ala in position 7; the peptide ring is then again closed, giving the [5-L-Thr(($\Psi^{R1,R2}$pro)]CsA derivatives of Cyclosporin A.

The derivatives of formula IIIa and IIIb were prepared by reaction with the appropriate Fmoc-NMeLeu-L-Thr($\Psi^{R1,R2}$pro)-OH dipeptide.

| Derivative | R$_1$ | R$_2$ |
|---|---|---|
| IIIa | H | MeO-PEG 750-NHCO-phenyl- |
| IIIb | Me | Me |

Figure 2:
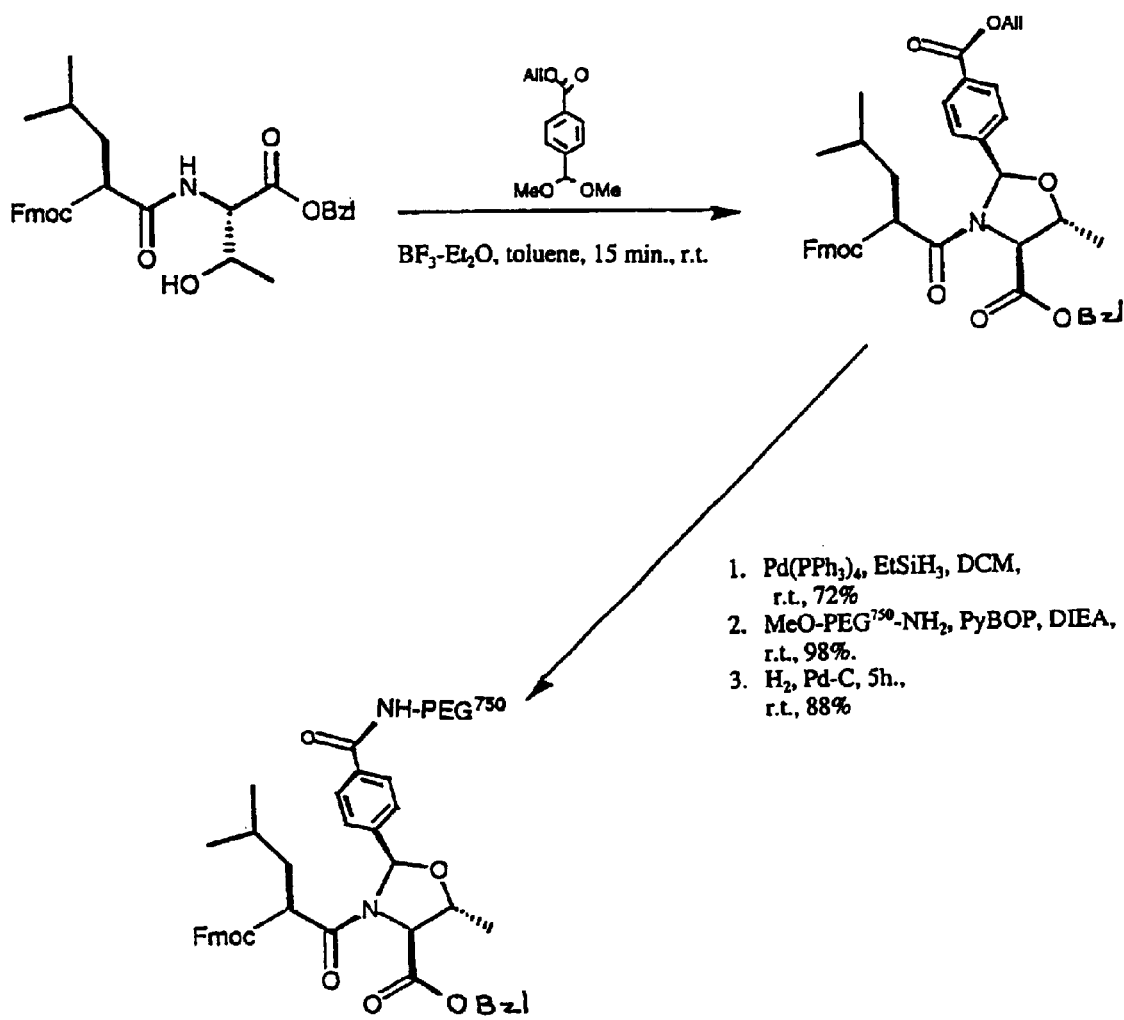
FIG. 2 shows the synthetic scheme for synthesis of an intermediate in the preparation of the derivative of FIG. 1.

The synthetic schemes for the synthesis of derivative IIIa, and of one of the intermediates in this synthesis, the dipeptide Fmoc-NMeLeu-L-Thr($\Psi^{MeO-PEG-750-NHCO-phenyl-H}$pro)-OH, are shown in detail in FIGS. 1 and 2. It appears that such a procedure, involving opening of the Cyclosporin A ring, insertion of a peptide containing the appropriate pseudo-proline, and ring closure, although it yields the derivatives of the present invention, is not suitable, on account of its complexity, for preparation of a large number of derivatives and on a large scale.

We give below practical details of the method of preparation of cyclosporin derivatives in the present invention. This uses as the starting material a cyclosporin in which the peptide chain comprises at least one of the amino acids serine, threonine and cysteine.

In a single stage involving an N,O-acetalisation of at least one of the three above-mentioned amino acids, using an appropriate compound of formula II above, a cyclosporin derivative is obtained, in which pseudo-proline has replaced one of the amino acids serine, threonine or cysteine of the starting cyclosporin.

2. Preparation of L-Thr($\Psi^{R1,R2}$pro)]CsC Derivatives of Cyclosporin C Having the General Formula IV:

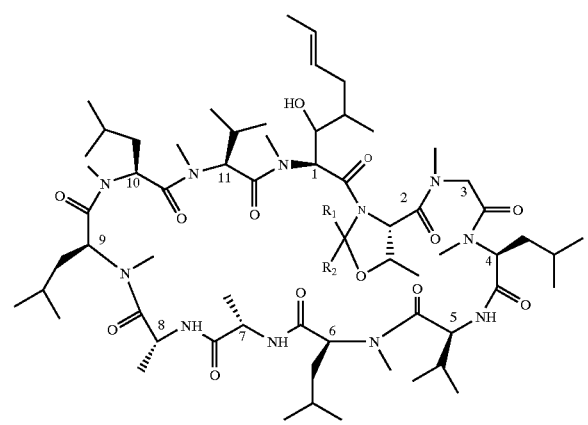

(IV)

The derivatives IVa to IVh were prepared by the following general method.

A mixture of anhydrous Cyclosporin C (CsC) (50 mg, 41 μmol), dimethylacetal $R_1R_2C(OMe)_2$(205 μmol, 5 eq) and pyridinium salt of p-toluenesulfonic acid (4.0 mg, 0.4 eq, PPTS) in anhydrous toluene (4 ml) is brought to reflux. When the reaction is complete, the organic phase is washed with $Na_2CO_3$ (10%, 2×5 ml) and water (2×5 ml), and dried over magnesium sulfate. The organic phase is concentrated under reduced pressure to yield an oil. The crude product is dissolved in 2 ml of an acetonitrile/water mixture (1:1 v/v) and purified by reverse-phase HPLC ($C_{18}$, 60–100% B, 40 min.). Lyophilisation gives the Cyclosporin C derivative as a white powder.

| Derivative | $R_1$ | $R_2$ | Reaction time (min.) | Yield (%) | Mass (calc.) found m/z | |
|---|---|---|---|---|---|---|
| IVa | H | Ph- | 45 | 74 | (1306.7) | 1306.7 |
| IVb | H | Ph-Ph- | 30 | 89 | (1382.8) | 1383.8 |
| IVc | H | CH2=CH— | 60 | 75 | (1256.7) | 1257.7 |
| IVd | H | p-$CO_2$Me-Ph- | 120 | 55 | (1364.7) | 1364.7 |
| IVe | H | p-OMe-Ph- | 60 | 90 | (1336.2) | 1337.2 |
| IVf | H | p-AllOOC-Ph- | 50 | 95 | (1390.7) | 1391 |
| IVg | H | p-HOOC-PhCH(OMe)$_2$ | 50$^d$ | 75 | (1350.7) | 1351 |
| IVh | H | PEG$^{850}$-CH— | 240 | 20 | (~1851) | ~1851$^e$ |

3. Preparation of D-Ser$^8$($\Psi^{R1,R2}$pro)]CsA Derivative of D-Ser$^8$-Cyclosporin A of General Formula V:

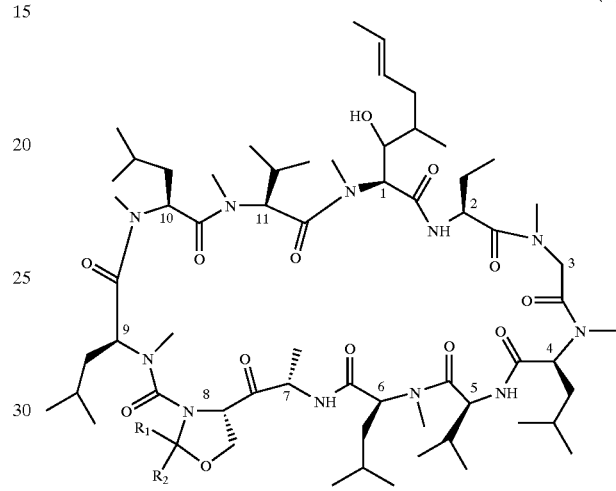

(V)

The derivatives Va to Ve were prepared by the following general method.

A mixture containing (anhydrous) Cyclosporin D-Ser$^8$-CsA (1 eq.), dimethylacetal $R_1R_2C(OCH_3)_2$ (10 eq.), PPTS (pyridinium salt of p-toluenesulfonic acid) (0.4 eq.) and anhydrous DMSO (0.016 M) is heated to 100°. The reaction mixture is poured into 150 ml of AcOEt. The organic phase is washed successively with a saturated solution of $NaHCO_3$ (3 times) and a saturated solution of NaCl (once), dried over $Na_2SO_4$ and concentrated. The crude product is purified by chromatography on silica gel (acetone/hexane, 4/6) to give a white powder.

| Derivative | $R_1$ | $R_2$ | Reaction time | Yield (%) | Rf (acetone/hexane) (4/6) | HPLC in minutes | Mass ESI-MS |
|---|---|---|---|---|---|---|---|
| Va | $CH_3$ | $CH_3$ | 3 h | 58 | 0.25 | 17.98 | 1244/1276/1293 |
| Vb | —$CH_2$OAc | H | 30 h | 74 | 0.32 | 18.65 | 1334/1351 |
| Vc | —(CH$_2$)—NH-Fmoc | H | 2 h | 70 | 0.25 | 17.96 | 1509/1526 |
| Vd | —Ph | H | 3 h | 72 | 0.50 | 19.16 | 1306/1323/1328 |
| Ve | -p-Ph—CH$_2$—NH-Aloc | H | 20 mn | 67 | 0.54 | 19.42 | 1419/1436 |

4. Physical Properties of the Cyclosporin Derivatives of the Present Invention.

4.1 Preparation of Prodrugs

Surprisingly, it has been found that introduction of a pseudo-proline within the cyclosporin chain allows preparation of a prodrug of the same cyclosporin.

The chemical stability of the derivatives of the present invention, particularly under acid hydrolysis conditions, has been studied as a function of the type of groups in the para position of the phenyl ring of the substituent $R_1$ or $R_2$. Electron-withdrawing groups stabilize the oxazolidine ring of the pseudo-proline. On the other hand, electron-donating groups, such as the methoxy group, make the pseudo-proline extremely sensitive to acid media and, in a reversible reaction, the oxazolidine ring opens, releasing the serine or threonine of the initial cyclosporin.

Figure 3:
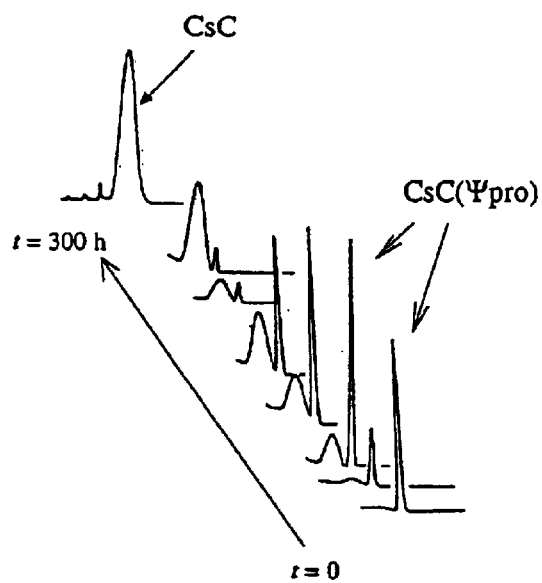
FIG. 3 shows HPLC chromatograms over a period of time in a hydrolysis test of a cyclosporin derivative.
Figure 4:
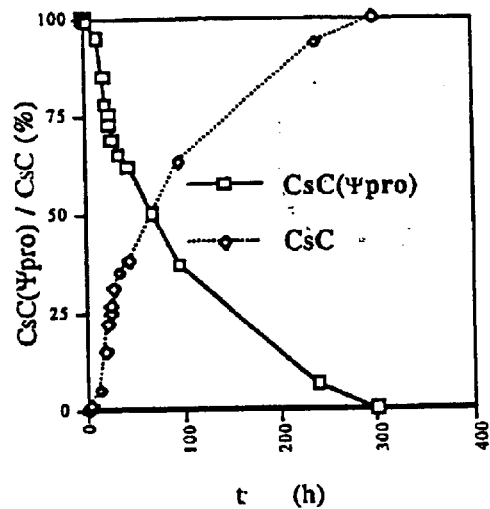
FIG. 4 is a curve showing the variation with time of the concentration of the products in the same hydrolysis test.

For example, derivative IVd, obtained from Cyclosporin C, was subjected to physiological conditions similar to those found in the digestive apparatus (pH 1, THF/HCl). As shown In FIGS. 3 and 4, the cyclosporin was entirely reconstituted in 300 hours.

4.2 Preparation of Hydrophilic Derivatives

Attachment of a polymer that is highly water-soluble, such as the polyethylene glycol in the IIIb and IVh derivatives, suppressed the hydrophobic character of the initial cyclosporins (Cyclosporin A and C respectively.)

5. Biological activity of the cyclosporin derivatives of the present invention; inhibition effect on calf thymus Cyclophilin A.

The binding test described by Fisher et al. in *Biomed. Biochim. Acta*, 1984 for cis-trans isomerases was applied to cyclophilin from calf thymus (3.8 nm), using the binding of Cyclosporin A as a reference. The values of the ratio $IC_{50}/IC_{50CSA}$ are shown in the table below.

| Derivatives | IIIb | IVa | IVb | IVc | IVd | IVe | IVf | IVg | IVh |
|---|---|---|---|---|---|---|---|---|---|
| $IC_{50}/IC_{50CSA}$ | 3.2 | 6 | 5.8 | 5.3 | 7.8 | 15.4 | 4 | 24.1 | 21.5 |

Figure 5:
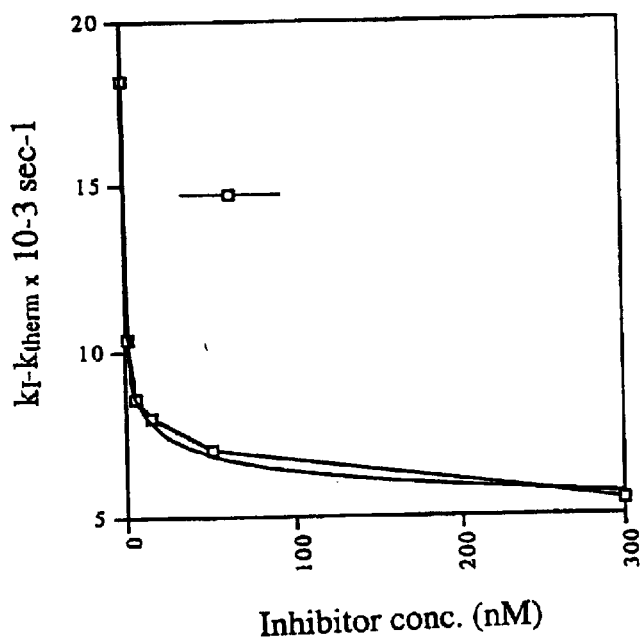
FIG. 5 is a curve showing the kinetics of inhibition, by a cyclosporin derivative, of cis-trans isomerase activity in Cyclophilin A from calf thymus.

The curve for inhibition of cis-trans isomerase activity of Cyclophilin A by the derivative IVb is shown in FIG. 5.

Surprisingly, despite the substantial modifications, such as steric modifications or fixing of the configuration of the peptide linkages, resulting from introduction of a pseudo-proline into the peptide moiety of Cyclosporins A or C that is assumed to bond to cyclophilin, there was no significant loss of activity in most of the derivatives, particularly for Iib, IVa-d and IVf. In fact, derivatives such as IVb, in which the pseudo-proline carries the highly hydrophobic biphenyl substituent, inhibit cyclophilin relatively strongly.

It is evident that the cyclosporin derivatives of the present invention possess highly interesting properties.

Specifically, the introduction of a pseudo-proline carrying appropriate substituents permits one or more of the following effects:

improvement of the pharmacokinetic properties of cyclosporins by solubilisation in a physiological medium;

production of "prodrugs" of the cydosporins;

introduction of reactive groups allowing crosslinking or labelling;

modulation of the peptide conformation of the cyclosporins on account of steric constraints due to the fivemembered ring, leading to modulation of the biological activity of the cyclosporins. -

What is claimed is:

1. A compound which is obtained by replacing at least one amino acid of a naturally-occurring cyclosporin with an amino acid of formula I:

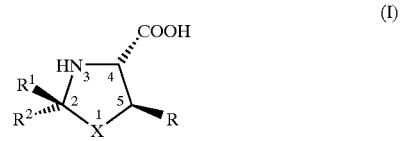

(I)

in which

X denotes an oxygen or a sulfur;

R denotes a hydrogen, or an alkyl group having between 1 and 6 carbon atoms;

$R^1$ and $R^2$ denote, independently of each other, a hydrogen, an alkyl group, having between 1 and 6 carbons, which may be straight-chain or branched-chain, substituted or non-substituted, an alkylene group having between 1 and 6 carbon atoms, a substituted or non-substituted aryl group, a substituted or non-substituted heteroaryl group, or $R^1$ and $R^2$ each independently denotes a residue of water-soluble polymer, wherein said polymer is optionally bonded to the carbon bearing $R^1$ and $R^2$ via a spacer group.

2. The compound according to claim 1, wherein in the amino acid of formula I, R denotes a hydrogen or a methyl group.

3. The compound according to claim 1, which is derived from a cyclosporin in which the peptide chain contains at least one amino acid, chosen from serine, threonine and cysteine, in D or L configuration.

4. The compound according to claim 3, wherein at least one of the amino acids serine, threonine or cysteine of the cyclosporin is replaced by the amino acid of formula I.

5. The compound according to claim 2, which is derived from a cyclosporin in which the peptide chain contains at least one amino acid, chosen from serine, threonine and cysteine, in D or L configuration.

6. A cyclosporin derivative in which the peptide chain comprises at least one residue of an amino acid of formula I:

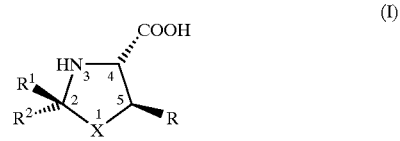

(I)

in which

X denotes an oxygen or a sulfur;

R denotes a hydrogen, or an alkyl group having between 1 and 6 carbon atoms;

$R^1$ and $R^2$ denote, independently of each other, a hydrogen, an alkyl group, having between 1 and 6 carbons, which may be straight-chain or branched-chain, substituted or non-substituted, an alkylene group having between 1 and 6 carbon atoms, a substituted or non-substituted aryl group, a substituted or non-substituted heteroaryl group, or $R^1$ and $R^2$ each independently denotes a residue of a water-soluble polymer, wherein said polymer is optionally bonded to the carbon bearing $R^1$ and $R^2$ via a spacer group, and which cyclosporin derivative is effective to inhibit cis-trans isomerase activity of cyclophilin A.

7. The derivative according to claim 6, wherein in the amino acid of formula I, R denotes a hydrogen or a methyl group.

8. The derivative according to claim 6 which is derived from a cyclosporin in which the peptide chain contains at least one amino acid, chosen from serine, threonine and cysteine, in D or L configuration.

9. The derivative according to claim 8, wherein at least one of the amino acids serine, threonine or cysteine of the cyclosporin is replaced by the amino acid of formula I.

10. The derivative according to claim 7 which is derived from a cyclosporin in which the peptide chain contains at least one amino acid, chosen from serine, threonine and cysteine, in D or L configuration.

11. A cyclic undecapeptide cyclosporin derivative in which the peptide chain comprises at least one residue of an amino acid of formula I:

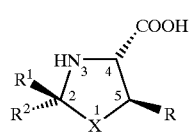

(I)

in which
X denotes an oxygen or a sulfur;
R denotes a hydrogen, or an alkyl group having between 1 and 6 carbon atoms;
$R^1$ and $R^2$ denote, independently of each other, a hydrogen, an alkyl group, having between 1 and 6 carbons, which may be straight-chain or branched-chain, substituted or non-substituted, an alkylene group having between 1 and 6 carbon atoms, a substituted or non-substituted aryl group, a substituted or non-substituted heteroaryl group, or $R^1$ and $R^2$ each independently denotes a residue of a water-soluble polymer, wherein said polymer is optionally bonded to the carbon bearing $R^1$ and $R^2$ via a spacer group.

12. The derivative according to claim 11, wherein in the amino acid of formula I, R denotes a hydrogen or a methyl group.

13. The derivative according to claim 11, which is derived from a cyclosporin in which the peptide chain contains at least one amino acid, chosen from serine, threonine and D or L configuration.

14. The derivative according to claim 13, wherein at least one of the amino acids serine, threonine or cysteine of the cyclosporin is replaced by the amino acid of formula I.

15. The derivative according to claim 12 which is derived from a cyclosporin in which the peptide chain contains at least one amino acid, chosen from serine, threonine and cysteine, in D or L configuration.

* * * * *